US005651046A

United States Patent [19]
Floyd et al.

[11] Patent Number: 5,651,046
[45] Date of Patent: Jul. 22, 1997

[54] ANATOMIC PHANTOM FOR EVALUATION OF PROJECTION RADIOGRAPHIC IMAGING SYSTEMS

[75] Inventors: Carey E. Floyd; Harrell G. Chotas, both of Durham, N.C.

[73] Assignee: Duke University, Durham, N.C.

[21] Appl. No.: 493,838

[22] Filed: Jun. 22, 1995

[51] Int. Cl.⁶ ............................................. G01D 18/00
[52] U.S. Cl. ................................... 378/207; 378/210
[58] Field of Search ..................................... 378/207

[56] References Cited

U.S. PATENT DOCUMENTS

| | | | |
|---|---|---|---|
| 4,126,789 | 11/1978 | Vogl et al. | 250/505 |
| 4,323,782 | 4/1982 | Riihimaki et al. | 250/252 |
| 4,550,422 | 10/1985 | VanPelt et al. | 378/207 |
| 4,638,502 | 1/1987 | Yaffe | 378/207 |
| 4,649,561 | 3/1987 | Arnold | 378/207 |
| 4,759,045 | 7/1988 | Lasky | 378/37 |
| 4,794,631 | 12/1988 | Ridge | 378/207 |
| 5,236,363 | 8/1993 | Sandrik et al. | 434/267 |
| 5,276,726 | 1/1994 | Galkin | 378/207 |

*Primary Examiner*—Craig E. Church
*Attorney, Agent, or Firm*—Richard E. Jenkins, P.A.

[57] ABSTRACT

An anatomic X-ray phantom having two layers of radiolucent material, at least one layer of metallic material therebetween, and a test pattern. The metallic layer is of a shape regionally similar to a corresponding human anatomy portion and has X-ray absorptive characteristics similar to the corresponding human anatomy portion. The test pattern is for X-ray quality assurance testing of the imaging system and is positioned inside the phantom in an area having radiopacity/radiolucency characteristics similar to the corresponding human anatomy portion. Other metallic layers also may be disposed between the two radiolucent layers. Preferably, the test pattern is directly adhered to a metallic layer on the side thereof facing the direction of the source of X-ray photons from the X-ray system.

9 Claims, 7 Drawing Sheets

ANATOMIC PHANTOM FOR EVALUATION OF PROJECTION RADIOGRAPHIC IMAGING SYSTEMS

TECHNICAL FIELD

The present invention relates, in general, to an X-ray phantom. More particularly, the present invention relates to an anatomic X-ray phantom adapted to measure a variety of operating parameters of an X-ray imaging system and provide information to an X-ray imaging equipment technician to enable the technician to test X-ray imaging equipment and to ensure that such equipment operates properly and in accordance with certain safety measurements. Especially, the present invention contemplates that the X-ray phantom will produce a "clinical" image wherein the X-ray phantom resembles the selected human anatomy portion sufficiently to cause the X-ray imaging system to respond as it would under actual clinical conditions during the taking of X-rays of the corresponding actual selected human anatomy portion.

BACKGROUND OF THE INVENTION

As is well known, an X-ray beam emanating from an X-ray tube may be passed through a selected portion of a patient to produce a shadow image of the internal structure of the patient on X-ray film. For quality assurance testing of X-ray imaging equipment and for teaching aids in training technicians, nurses, and the like in how to use X-ray imaging equipment, X-ray phantoms are well known. Prior art X-ray phantoms are available in a number of variations. Selected phantoms comprise plastic replicas of the human body or specific body portions, whereas other phantoms comprise actual human bones cast in plastic.

More particularly, an X-ray phantom is typically composed of a material that mimics human tissue in its ability to produce absorption and scattering of radiation, i.e., mimics radiopacity/radiolucency characteristics of human anatomy. The ability to absorb and scatter radiation is expressed by the attenuation coefficient, which is a function of chemical elements of which the material is composed and the spectrum of energies used in the X-ray examination. Variations of attenuation coefficients and thicknesses among materials produce contrast in an X-ray image. Two substances with the same attenuation coefficient and thickness will similarly absorb and scatter X-rays under given imaging conditions and will produce the same contrast with respect to a third substance during an X-ray examination. Many prior art phantoms include calibration patterns or test patterns consisting of metal objects (for instance, solid circles, hollow circles, and/or parallel lines) for assisting the technician in providing adjustments in the X-ray system with respect to optical density, spatial resolution, and contrast-detail.

One example of an X-ray phantom is shown in U.S. Pat. No. 4,794,631 to Ridge. This patent describes a cardiovascular phantom including a sandwich of circuit boards and plates encapsulated within an acrylic block. Specifically, 6 circuit boards have a lead coating that is etched away to provide the arborescent appearance of major arteries, and also each circuit board contains a space therein to allow for the lung field. A copper plate is included in the phantom and has an opening therein analogous to the spaces in the circuit boards for creating the lung field, and a copper diaphragm plate is provided.

An X-ray phantom is described in U.S. Pat. No. 4,126,789 to Vogl et al. This patent describes a phantom having a radiolucent sealed case of a high impact plastic material, such as polycarbonate, and containing body part objects, such as a genuine femur, suspended in salt water. Other objects in the phantom include traditional X-ray machine evaluation and calibration devices, such as a resolution test pattern of spaced metal bars (i.e., parallel lines), a step wedge penetrometer, and a wire mesh test pattern.

Another phantom is shown in U.S. Pat. No. 4,323,782 to Riihimaki et al. which describes a human skull phantom that includes an aluminum cylinder with a wall thickness of about 3 mm so that the absorption in the cylinder corresponds to the absorption in the bones of a human skull. The cylinder has on its respective ends two end caps made of acrylic plastic. Smaller vessels, also cylindrically shaped, are contained within the cylinder. An image can be taken of the phantom with an X-ray computed tomography system in which can be seen small circles corresponding to the small vessels. Then, another image can be made by placing the phantom into another X-ray computed tomography system. The resultant images are compared with each other to see whether an equal number of the smaller vessels can be seen, and if so, then the absorption resolutions of both tomography systems are determined to be equally good.

An angiographic X-ray phantom for use with digital X-ray equipment is disclosed in U.S. Pat. No. 4,649,561 to Arnold. The phantom is representative of human tissue containing variable concentrations of iodine and serves as a test device for assessing the performance of X-ray imaging systems such as digital subtraction angiographic apparatus. The phantom contains a test pattern including disc details and elongated cylindrical details, with all details being provided in varying iodine concentrations and the elongated details also being provided in varying diameter cross-sections simulating arterial and venous configurations.

Also of interest with respect to X-ray phantoms, typically including test patterns, are U.S. Pat. No. 4,097,793 to Shapiro et al.; U.S. Pat. No. 4,550,422 to VanPelt et al.; U.S. Pat. No. 4,578,767 to Shapiro; U.S. Pat. No. 4,638,502 to Yaffe; U.S. Pat. No. 4,759,045 to Lasky; U.S. Pat. No. 4,818,943 to Chandra; U.S. Pat. No. 5,063,583 to Galkin; U.S. Pat. No. 5,236,363 to Sandrik et al.; and U.S. Pat. No. 5,276,726 to Galkin.

It should be noted that all of the above-described phantoms except Arnold are designed for use with analogue X-ray systems. Even though the X-ray phantom described in the above-mentioned U.S. Pat. No. 4,649,561 to Arnold is intended for use with a digital X-ray system, the parts of that phantom do not radiographically resemble human anatomy parts. Thus, none of the prior art X-ray phantoms addresses the increasing need, which has resulted from the increasing use of digital imaging X-ray systems with automated, examination-specific, and content-sensitive image processing techniques, for a class of phantoms that radiographically resemble human anatomy and provide X-ray images with features useful for objective quality assurance evaluation of the digital X-ray imaging system.

To be more specific, conventional analogue projection radiographic imaging systems use a screen-film sandwich to detect X-ray photons and to create a radiographic image on the film. For a given incident X-ray energy, these conventional image receptors possess fixed characteristics including X-ray sensitivity, latitude (i.e., dynamic range, which is the range of X-ray exposures that can be accurately recorded in an image), contrast, spatial resolution, and noise. Conventional receptors, therefore, can be thought of as static systems in which the properties of the imaging system are not dependent on image content. Additionally, for a given X-ray energy (kilovoltage peak, abbreviated herein as kVp), only a narrow range of acceptable exposure settings exist that will produce an acceptable film image. An underexposed conventional film is too light (transparent) whereas an over-exposed film is too dark. Both conditions make the resultant films undesirable for diagnostic use.

Because the properties of conventional analogue radiography systems do not depend on image content, various test objects that do not produce a radiographic image shape that resembles the corresponding human anatomy part, as can be seen from a review of the above-described patents involving X-ray phantoms, often have been used. If the phantom contains a test pattern, typically used are step wedges (such as stair-step-like objects of increasing thickness which, when radiographed, produce a series of nearly-uniform film areas with decreasing optical densities), line resolution phantoms that can be visually evaluated to estimate the smallest visible structure on film, and contrast detail phantoms consisting of objects of decreasing size and contrast (circles and/or parallel lines) which can be visually evaluated to assess barely detectable features in the image on the film.

Unlike analogue X-ray imaging systems, in which the film serves as both detector and display medium, digital X-ray imaging systems employ a multi-stage process that separates X-ray detection from image display. In digital systems, X-rays are first detected by a receptor (typically a wide-latitude receptor), and the image is converted to a matrix of digital values (known in the art as pixels) which correspond to X-ray intensity at each position in the image. Later, the digital image data are computer processed and then transformed back into analogue form for display, typically on laser-printed film or on a video monitor such as at a diagnostic workstation.

The separation of digital image detection and display makes possible a wide variety of capabilities that are not possible with analogue screen-film systems, including, but not limited to:

(1) The capability to use a wide range of X-ray exposure levels in the acquisition of an image, without causing the final film image to be too dark or too light because digital systems typically employ a wide-latitude image receptor;

(2) The capability to analyze automatically the digital image data in an effort to identify the useful exposure range so as to optimize contrast resolution that affects final image quality; and (3) The capability to digitally process the image in different ways, for instance, enhancing contrast and/or spatial resolution, reducing noise, and the like, for optimum visualization of key features as needed for specific diagnostic tests.

Each of the three above-mentioned capabilities of digital X-ray imaging systems can change the appearance of the radiographic image produced from the phantom. For example, variations in X-ray exposure level produce changes in the signal-to-noise ratio in the image, which can ultimately affect object detectability. Also, image processing can change the image appearance in any number of subtle ways, depending on the operations performed.

Commercial digital radiographic imaging systems are programmed to perform these operations conditionally, in ways that depend on the nature of the image itself, i.e., the image content. Typically, the behavior of the X-ray imaging system is determined by the histogram of the digital data within the full image or a prescribed image subregion. Since the histogram of human anatomy is quite different from that of most non-anatomic radiographic test pattern objects, images of anatomy and non-anatomic test pattern objects can be expected to be processed quite differently. Accordingly, it is not possible from examining the properties of the resultant film of a radiograph of a step wedge to infer anything about how a subsequent chest image produced by the same X-ray imaging system would appear.

Therefore, a need exists for the ability to evaluate image quality, particularly digital image quality, and to evaluate the ability of an X-ray imaging system, particularly a digital imaging system, to produce a clinical image. The X-ray phantom should resemble human anatomy in both average radiographic density and appearances (possessing both a shape regionally similar to that of the corresponding real human anatomy portion and a histogram similar to that of the corresponding real human anatomy portion), and also should contain designated test pattern region(s) for optical density measurements, spatial resolution, and contrast-detail measurements, all without unduly changing the "human-like" qualities of the resultant overall image. Applicants have developed a phantom to meet the long-felt need for such a phantom.

SUMMARY AND OBJECTS OF THE INVENTION

Accordingly, the present invention provides an improved X-ray phantom generally useful with X-ray imaging systems, either analogue or digital, but in particular, useful with digital X-ray imaging systems. The phantom comprises an anatomic X-ray phantom having two layers of radiolucent material, at least one layer of metallic material disposed between the two layers of radiolucent material, and at least one test pattern.

The metallic layer has a shape regionally similar to a corresponding human anatomy portion and has X-ray absorptive characteristics similar to the corresponding human anatomy portion. The test pattern is adapted for X-ray quality assurance of the X-ray imaging system when the phantom is in use with the X-ray imaging system and is positioned inside the phantom in an area having radiopacity/radiolucency characteristics corresponding to the anatomically equivalent area. Other metallic layers may be disposed between the two radiolucent layers.

Thus, it is an object of the present invention to provide an anatomic X-ray phantom, including a test pattern therein, which phantom can be used with an X-ray imaging system and provide information with respect to how an image of a real human anatomy portion corresponding to the portion in the phantom would appear when produced by the same X-ray imaging system.

It is another object of the present invention to provide an improved anatomic X-ray phantom particularly adapted for use with a computerized imaging system.

Some of the objects of the invention having been stated above, other objects will become evident as the description proceeds, when taken in connection with the accompanying drawings as best described below.

DETAILED DESCRIPTION OF THE INVENTION AND OF THE BEST MODE FOR CARRYING OUT THE INVENTION

Figure 1:
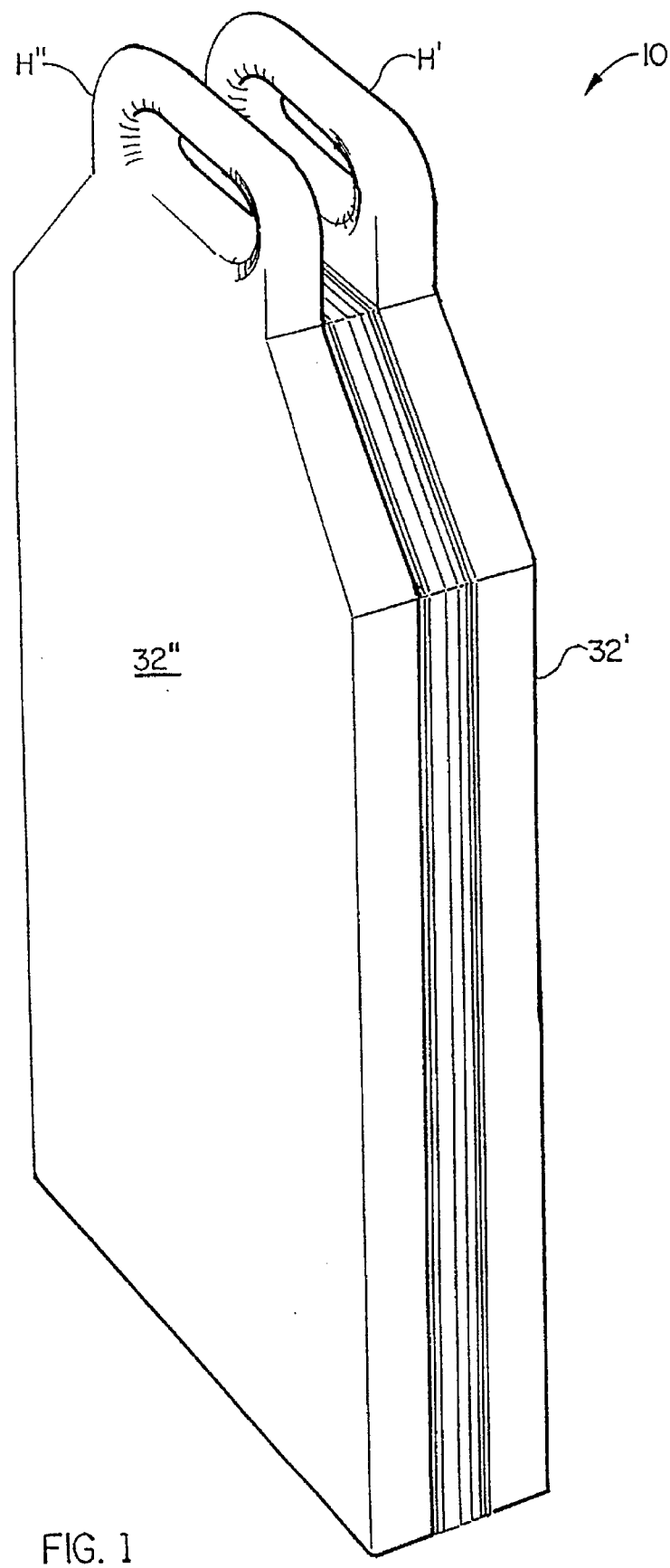
FIG. 1 shows a perspective view of the anatomic X-ray phantom of the invention.
Figure 2:
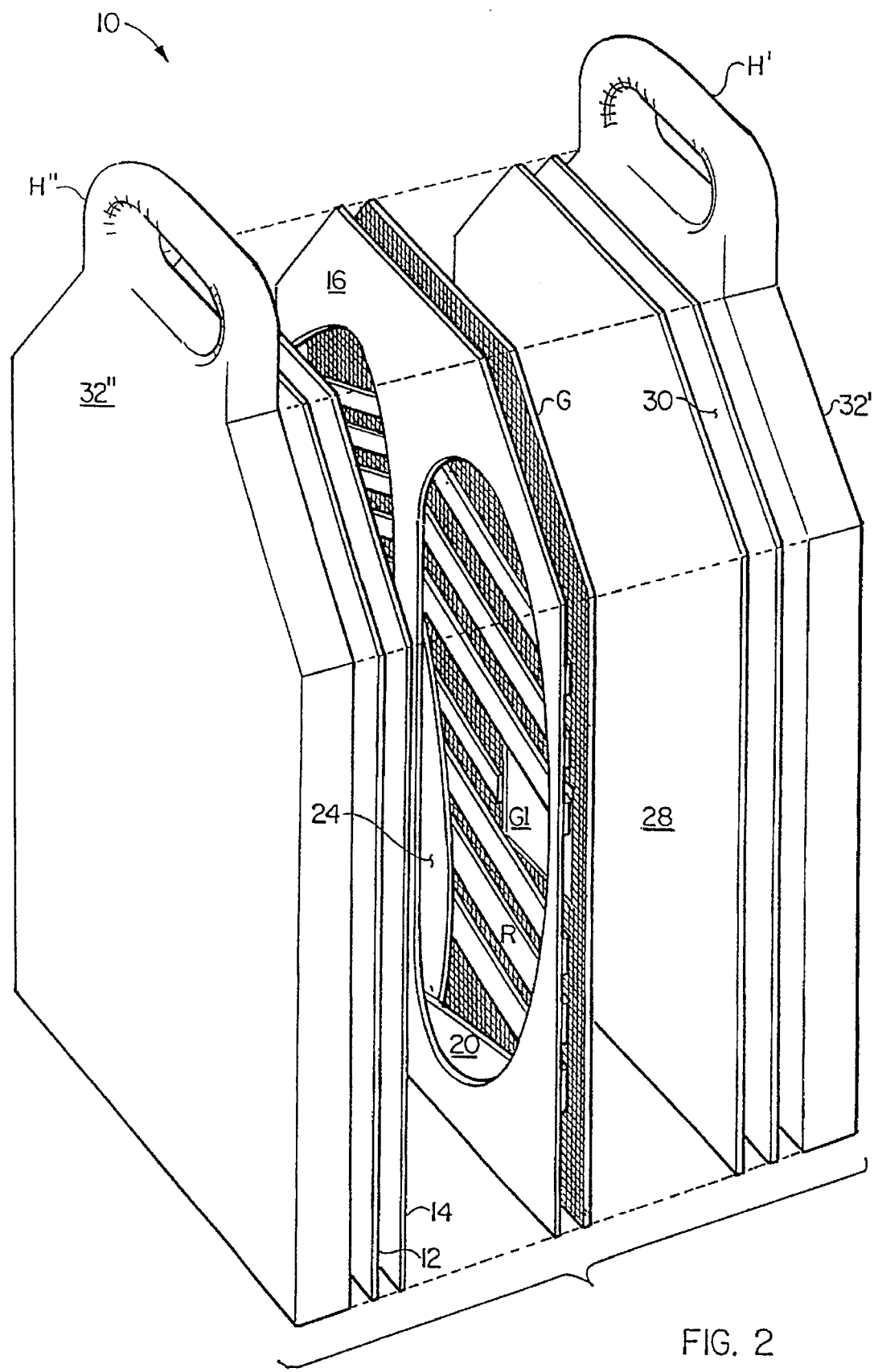
FIG. 2 shows a partially exploded perspective view of the phantom of FIG. 1.
Figure 3:
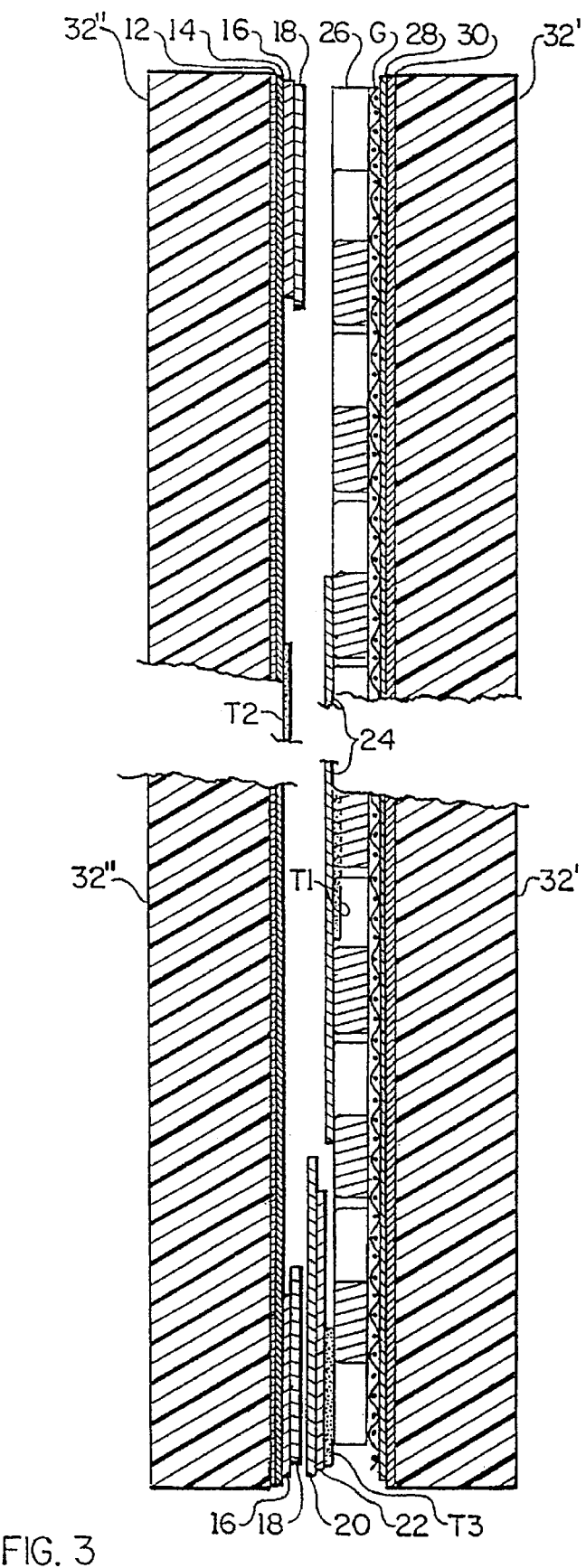
FIG. 3 shows a vertical cross-sectional view of the phantom of FIG. 1.
Figure 4:
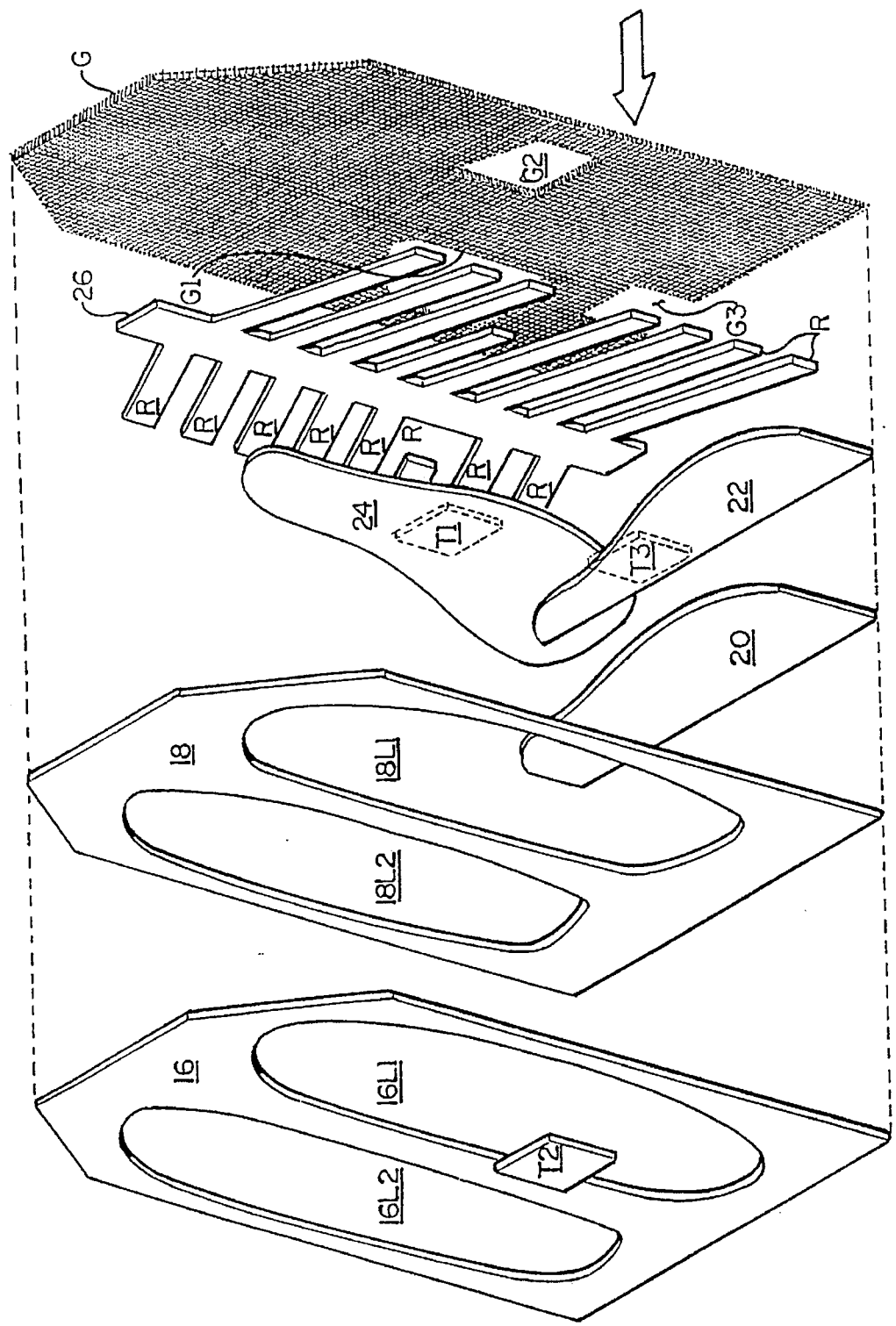
FIG. 4 shows a perspective exploded view of selected internal plates of the phantom of FIG. 1.
Figure 5:
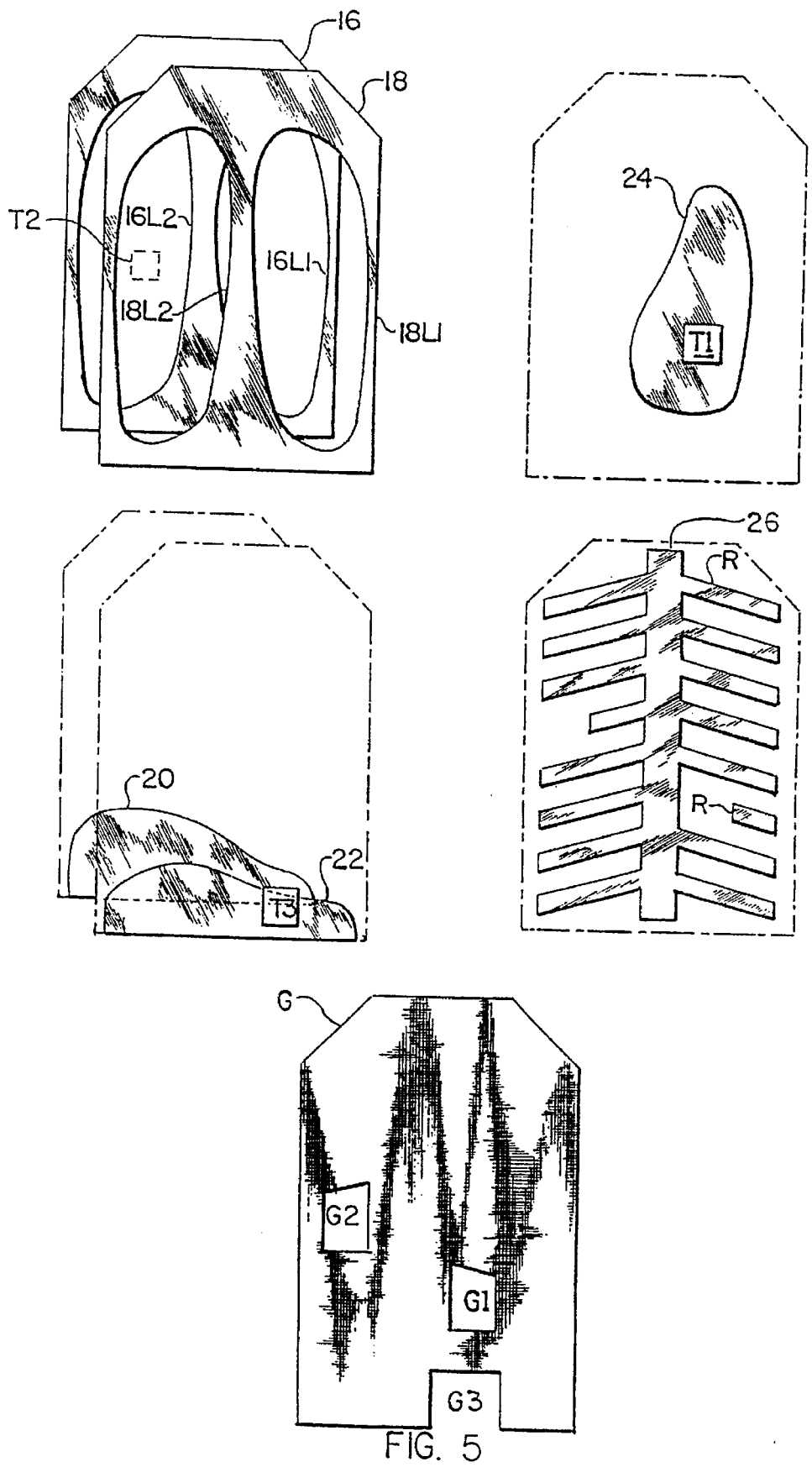
FIG. 5 shows individual side elevation views of each of the selected plates and of the grid shown in FIG. 4.

Looking particularly at FIGS. 1–5, shown is anatomic X-ray phantom 10 in a perspective view, a partially exploded view, and a vertical cross-sectional view, respectively, in FIGS. 1–3, and selected plates of phantom 10 in an exploded view and a side view, respectively, in FIGS. 4 and 5. Phantom 10 is illustrated having ten metal plates or layers 12, 14, 16, 18, 20, 22, 24, 26, 28, 30, with optional metal grid G disposed between layers 26 and 28, all arranged in a sandwich-like fashion (see FIG. 4) between radiolucent plates or layers 32', 32". Layers 12, 14, 16, 18, 20, 22, 24, 26, 28, 30, 32' and 32", and metal grid G, may be secured together in various conventional ways, such as by adhesive resins, screws and the like (not illustrated).

Also, phantom 10 is illustrated having three test patterns T1, T2, and T3 for X-ray quality assurance of an X-ray imaging system (not illustrated) when phantom 10 is in use with the system. Patterns T1, T2, and T3 are positioned inside phantom 10 in an area having radiopacity/radiolucency characteristics corresponding to that of a real heart, lung, and abdomen, respectively. Hence, test patterns T1, T2, and T3 are preferably positioned directly on (such as by a conventional adhesive) plates 24, 14, and 22 (see FIG. 4), which are, respectively, a heart plate, a lung backing plate, and an abdominal plate, as discussed in more detail below, on the side thereof that will be facing the direction of the emanation of X-ray photons (see arrow P in FIG. 4).

More specifically, when phantom 10 is in use with an X-ray imaging system (not illustrated), the beam of X-ray photons emanating from the X-ray system will travel in the direction of arrow P (see FIG. 4) and impinge on the components of phantom 10 in the following order: 32', 30, 28, G, 26, 24, 22, 20, 18, 16, 14, 12, 32", although other orders, particularly for components 28, G, 26, 24, 22, 20, 18, 16, 14, may be suitable.

Although phantom 10 is illustrated in the preferred embodiment with 10 plates or layers and 3 test patterns, there may be more or fewer, depending on the selected body parts it is desired to simulate when taking an x-ray image employing phantom 10. Furthermore, although the particular phantom illustrated is a chest phantom, the invention contemplates other phantoms, such as an abdominal and a head phantom (i.e., a skull-brain phantom).

Each of plates 16, 18, 20, 22, 24, 26 is made of a metal having absorptive characteristics of the human anatomy portion (not illustrated) to which it corresponds. Each of plates 12, 14, 28, 38 is also made of the same kinds of metals. Suitable metals include, but are not limited to, copper, aluminum, vanadium, and titanium, as well as the iron alloy, stainless steel. It is noted that by reference to copper, aluminum, vanadium, and titanium, it is intended also to include alloys thereof. Although applicants have described plates 12, 14, 16, 18, 20, 22, 24, 26, 28 and 30 as formed of metal, applicants contemplate that the anatomically equivalent internal components of phantom 10 may be formed of any material having absorptive characteristics of the human anatomy portion to which it corresponds.

Grid G is suitably made of 20 mesh stainless steel and serves the purpose of providing visual information over the entire field regarding sharpness when a technician or other worker is focusing an X-ray system for taking X-rays of phantom 10. More particularly, grid G serves to break up uniform transmission areas from the metal plates or layers, and is particularly useful for when the X-ray system is digital, as the pixels and histogram will change. For instance, system sensitivity and/or latitude can be assessed in storage-phosphor systems and automatic exposure control devices can be tested, where such capabilities are part of the system.

Each of radiolucent plates 32', 32" is suitably made of material radiolucent to X-rays, a typical material being a polycarbonate, such as an acrylic polymer, for instance the acrylic polymer sold under the trademark LUCITE®. Other materials include, but are not limited to, polyurethanes and fiberglass. In addition to plates 32', 32" being of a material that is radiolucent to X-rays, the only other requirement of the material is that it be sufficiently rigid to provide dimensional stability for phantom 10 and to assist in holding metal plates 12, 14, 16, 18, 20, 22, 24, 26, 28, 30, and grid G, in place.

Phantom 10 is shown with optional handles H', H" (which could be one unitary handle, not illustrated) integral with plates 32', 32", respectively, for ease of carrying phantom 10, which is relatively small, lightweight, and portable.

If desired, anatomic X-ray phantom 10 may suitably have an aluminum support frame (not illustrated) provided around the sides thereof, and then the support frame may conveniently include handle(s), rather than including handles H1, H2 integral with radiolucent layers 32', 32".

The particular phantom 10 constructed is 14 inches (35.6 cm) wide, 17 inches (43.2 cm) tall, and 2.5 inches (6.35 cm) thick, with plates 32', 32" each being 1 inch (2.54 cm) thick and remaining sandwiched components 12, 14, 16, 18, 20, 22, 24, 26, G, 28, 30 together having a thickness of 0.5 inches (1.27 cm). This size is suitable for radiographing in the conventional 14 inch×17 inch format (35.6 cm×43.2 cm format), although other sizes may be employed and it is not intended to limit the phantom of the invention to the particular sizes described here. The X-ray attenuation of phantom 10 is equivalent to that of a large human chest of a 200 pound (90 kg) human in the frontal orientation (postero-antero or antero-postero) at diagnostic energies approximately 80 to about 140 kVp.

Referring particularly now to FIGS. 4 and 5, illustrated in detail are selected metal plates 16, 18, 20, 22, 24, 26 and grid G of FIG. 1 in a perspective exploded view and a side elevation view, respectively, to illustrate better the sequential layering relationship resulting in the above-mentioned sandwich construction. When phantom 10 is in use with an X-ray imaging system (not illustrated), the beam of X-ray photons emanating from the X-ray imaging system will travel in the direction of arrow P to contact grid G prior to contacting plates 26, 24, 22, 20, 18, and 16.

Plates 16, 18 define similarly shaped first and second lung outlines, suitably made of copper and having a thickness of 0.5 mm. To provide a lung field, first plate 16 is provided with reciprocal lung-shaped spaces 16L1, 16L2, and likewise, second plate 18 is provided with reciprocal lung-shaped spaces 18L1, 18L2. Each of spaces 16L1, 16L2, 18L1, 18L2 is generally about 12 inches×4.5 inches (about 30.5 cm×11.4 cm) in length and width. Although first and second lung-shaped outline plates 16 and 18 preferably have the same outside dimensions, spaces 16L1 and 18L1 are slightly different in size, and likewise, spaces 16L2 and 18L2 are slightly different in size. Two plates 16 and 18 with two different sized sets of spaces 16L1, 16L2 and 18L1, 18L2 are not necessary, as one plate with one set of spaces could be employed, but two are desired in order to create realistic shadows (see FIG. 7) in the resultant X-ray image so that it is analogous to the lung field from an image of a pair of real lungs.

Each of plates 20, 22 is a first and second abdomen-shaped plate, and made of copper that is 0.5 mm thick. Each is generally about 5 inches×13 inches (about 12.7 cm×33 cm) in length and width, but each is slightly different in size. Two abdominal-shaped plates 20, 22 are preferred for the same reason as mentioned above with respect to two lung-shaped outline plates 16, 18, in order to provide realistic shadows in the resultant X-ray image (see FIG. 7).

Heart-shaped plate 24 is also suitably made of copper and has a thickness of 0.5 mm. Plate 24 is generally about 7 inches×6 inches (about 17.8 cm×15.2 cm) in length and width. All of plates 20, 22, 24 are disposed between plate 18 and plate 26.

Plate 26 is a rib bones shaped plate, suitably made of aluminum and having a thickness of 0.635 cm. Plate 26 contains a plurality of ribs R, each about 0.50 inches (1.27 cm) in width and about 5.0 inches (12.7 cm) in length, and dimensioned to fit inside of lung spaces 16L1, 16L2, 18L1, 18L2, when the sandwich construction is placed together as shown in FIG. 1. Two of ribs R are partially cut away so that when phantom 10 is subjected to X-ray photons coming in the direction of arrow P from an X-ray system (not illustrated), the photons will impinge on test patterns T1, T2 without first passing through any of ribs R.

Grid G contains three open spaces G1, G2, G3 which are cut out of grid G in an appropriate size for reciprocal correspondence with heart test pattern T1, lung test pattern T2, and abdominal test pattern T3, respectively. Thus, when phantom 10 is subjected to X-ray photons coming in the direction of arrow P from an X-ray system (not illustrated), the photons will desirably impinge on test patterns T1, T2, T3 without first passing through the 20 gauge mesh of grid G.

Plate 14 and plate 28 (see FIG. 2) are similarly sized, completely solid (i.e., have no cut out spaces such as space 16L1 in plate 16) first and second backing plates for lung plates 16, 18. Each of first and second lung backing plates 14, 28 is suitably made of copper and has a thickness of 0.5 mm. Plate 14 is disposed between plate 12 and plate 16 and has test pattern T2 positioned thereon. Similarly, plate 28 is disposed between plate 26 and plate 30, or if grid G is present, then, the order of the plates is plate 26, grid G, plate 28, plate 30.

Plate 12 and plate 30 (see FIG. 2) are similarly sized, completely solid (i.e., have no cut out spaces such as space 16L1 in plate 16) first and second backing plates for the remainder of the sandwiched plates 14, 16, 18, 20, 22, 24, 26, 28, and grid G. Each of first and second backing plates 12, 30 is suitably made of aluminum and has a thickness of 1 mm. Plate 12 is disposed between plate 14 and radiolucent plate 32", and similarly, plate 30 is disposed between plate 28 and radiolucent plate 32'.

Figure 6:
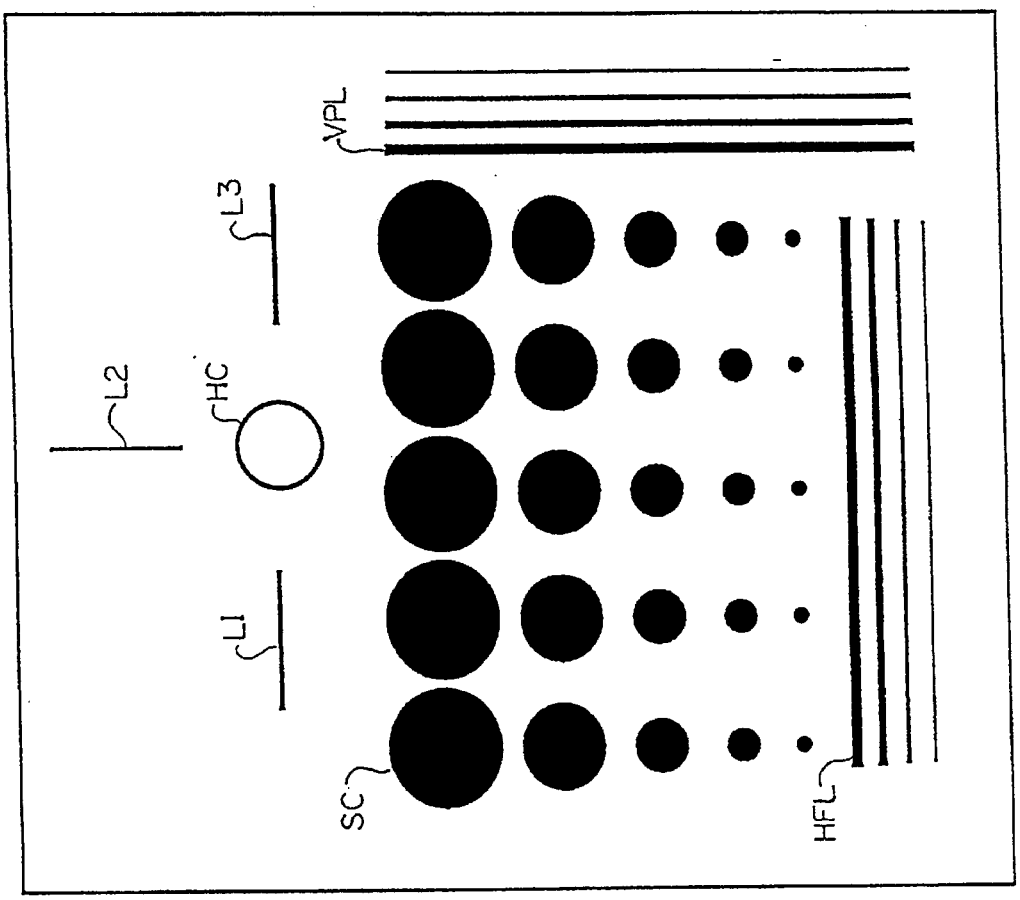
FIG. 6 shows a representative test pattern utilized in the anatomic X-ray phantom of FIG. 1.

With reference now to FIG. 6, illustrated is a representative test pattern T used as T1, T2, T3 herein. Test patterns are well known in the art of phantoms, and the particular diameters, lengths, thickness, amounts, and metals of the circles and lines therein can vary.

Test pattern T is about 1.50 inches (3.80 cm) in width and about 2 inches (5.08 cm) in length, and contains: (i) a hollow circle HC having partially radially disposed thereabout three equally-sized lines, L1, L2, L3, (ii) twenty-five solid circles SC arranged in five rows and five columns, (iii) four vertically disposed parallel lines VPL of equal length and diminishing thickness, and (iv) four horizontally disposed parallel lines HPL of equal length and diminishing thickness.

Each of hollow circle HC and lines L1, L2, L3 is suitably made of stainless steel. The thickness of the annular ring that forms hollow circle HC is 1.0 mm and the diameter of hollow circle HC is 4.5 mm. The length and thickness of each of lines L1, L2, L3, are 10 mm and 1 mm, respectively.

Solid circles SC are suitably made of copper. The diameters of solid circles SC in each row from the top row to the bottom row are 6 mm, 4.5 mm, 3 mm, 1 mm, and 0.5 mm, respectively. The thicknesses of solid circles SC for each column of the five columns is the same in a particular column, but thicknesses will vary depending on whether the particular test pattern T is pattern T1 disposed on heart plate 24, pattern T2 disposed on lung backing plate 14, or pattern T3 disposed on abdominal plate 22.

More specifically, for the particular test pattern T1 disposed on heart plate 24, the thicknesses from the left-hand column to the right-hand column are 0.5 mils, 1 mil, 2 mils, 3 mils, and 5 mils (12.7 microns, 25.4 microns, 50.8 microns, 76.2 microns, and 127 microns). For particular test pattern T2 disposed on lung backing plate 14, the thicknesses from the left-hand column to the right-hand column are 0.25 mil, 0.5 mil, 1 mil, 2 mils, and 3 mils (6.35 microns, 12.7 microns, 25.4 microns, 50.8 microns, and 76.2 microns). For the particular test pattern T3 disposed on abdominal plate 22, the thicknesses from the left-hand column to the right-hand column are 2 mils, 4 mils, 6 mils, 10 mils, and 16 mils (50.8 microns, 101.6 microns, 152.4 microns, 254 microns, and 203.2 microns).

The length of all lines VPL, HPL is 35 mm. The respective diminishing thicknesses, 0.6 mm, 0.3 mm, 0.2 mm, and 0.1 mm, are the same for the four lines VPL and the four lines HPL.

Figure 7:
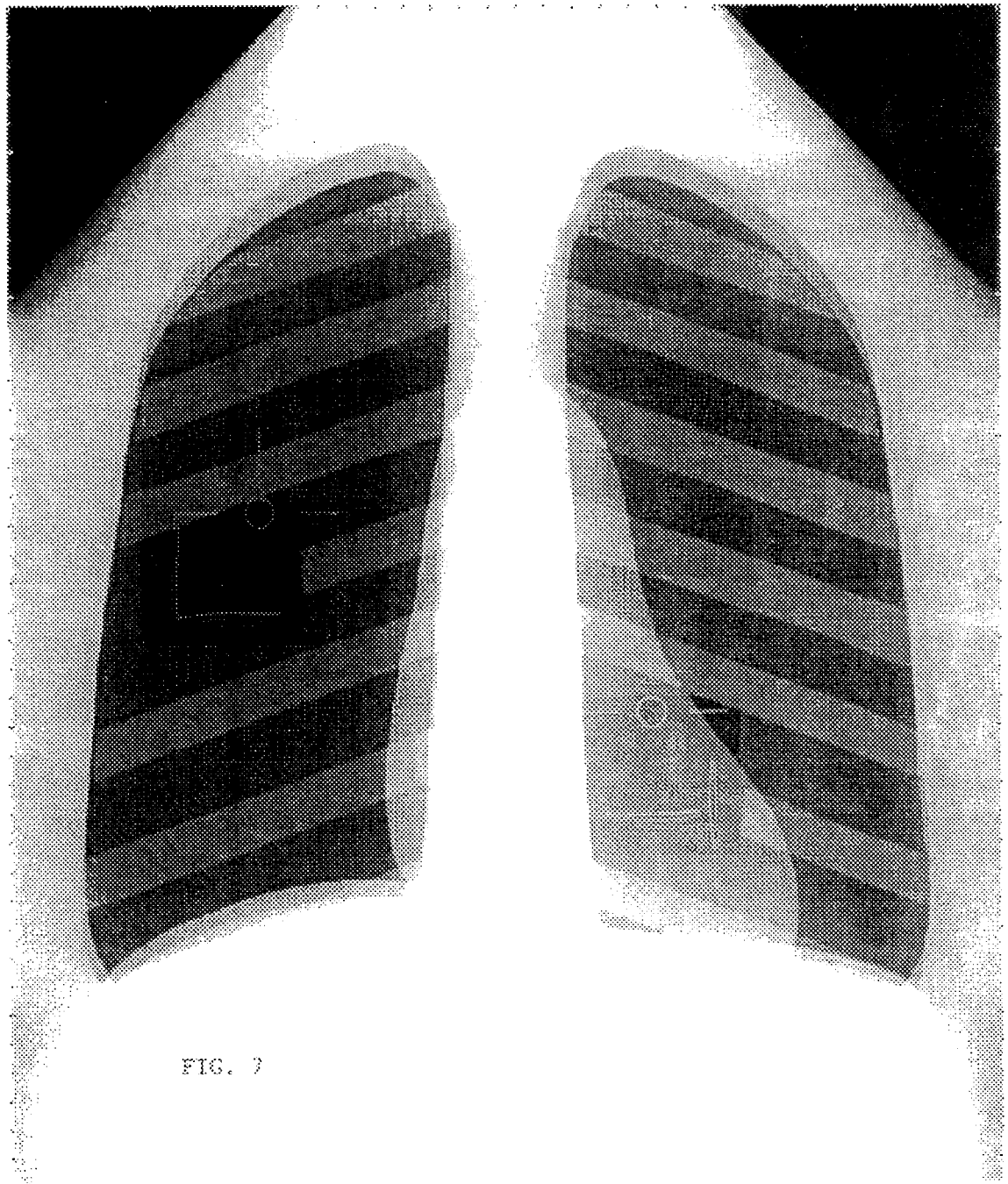
FIG. 7 is a print-out of an X-ray image taken of the phantom of FIG. 1.

FIG. 7 is a print-out of an actual X-ray image taken of phantom 10 of FIG. 1 using digital X-ray imaging equipment, and as can be seen, the X-ray image is realistic looking. More specifically, lung-shaped outline plates 16, 18, abdominal-shaped plates 20, 22, heart-shaped plate 24, and rib bones shaped plate 26, as well as test patterns T1, T2, T3, can all be readily seen. Additionally, as noted above, a realistic lung shadow can be seen because of the difference in size between spaces 16L1, 16L2 and spaces 18L1, 18L2. Likewise, a realistic abdominal shadow can be seen because of the two slightly different sized abdominal-shaped plates 20, 22.

Therefore, when the digital X-ray imaging system viewed phantom 10, the system saw phantom components of a shape regionally similar to corresponding human anatomy portions, whereby the pixels were automatically converted by the system to a realistic looking X-ray image. Hence, phantom 10 can be used with a digital X-ray imaging system to provide a realistic looking X-ray image and thus provide information with respect to how an image of a real human anatomy portion corresponding to the portion in phantom 10 would appear when produced by the same X-ray imaging system. Phantom 10 can also be used with analogue X-ray imaging equipment.

In use, applicants contemplate that for the taking of X-rays of phantom 10, three independent X-rays should first be taken to establish a baseline definition. Then, subsequent X-rays taken of phantom 10 can be compared therewith.

It will be understood that various details of the invention may be changed without departing from the scope of the invention. Furthermore, the foregoing description is for the purpose of illustration only, and not for the purpose of limitation—the invention being defined by the claims.

What is claimed is:

1. An anatomic X-ray phantom for use with an X-ray imaging system, comprising:
   (a) a radiolucent material;
   (b) at least one layer of material of a shape regionally similar to a corresponding human anatomy portion and having X-ray absorptive characteristics similar to the corresponding human anatomy portion, and being disposed within said radiolucent material;
   (c) at least one test pattern adapted for X-ray quality assurance of the X-ray system when the phantom is in use with the X-ray system and being positioned inside the phantom in an area having radiopacity/radiolucency characteristics similar to the corresponding human anatomy portion;
   (d) wherein the phantom contains a plurality of human anatomy-shaped metallic layers disposed within said radiolucent material in the following order: a first lung-shaped outline defining layer, a second lung-shaped outline defining layer, a first abdominal-shaped layer, a second abdominal-shaped layer, a heart-shaped layer, and a rib bones shaped layer; and
   (e) wherein the phantom further includes additional metallic layers and all metallic layers are disposed within said radiolucent material in the following order: a first backing layer, a first lung backing layer, a first lung-shaped outline defining layer, a second lung-shaped outline defining layer, a first abdominal-shaped layer, a second abdominal-shaped layer, a heart-shaped layer, a rib bones shaped layer, a second lung backing layer, and a second backing layer.

2. An anatomic X-ray phantom for use with an X-ray imaging system, comprising:
   (a) a radiolucent material;
   (b) at least one layer of material of a shape regionally similar to a corresponding human anatomy portion and having X-ray absorptive characteristics similar to the corresponding human anatomy portion, and being disposed within said radiolucent material;
   (c) at least one test pattern adapted for X-ray quality assurance of the X-ray system when the phantom is in use with the X-ray system and being positioned inside the phantom in an area having radiopacity/radiolucency characteristics similar to the corresponding human anatomy portion;
   (d) wherein the phantom contains a plurality of human anatomy-shaped metallic layers disposed within said radiolucent material in the following order: a first lung-shaped outline defining layer, a second lung-shaped outline defining layer, a first abdominal-shaped layer, a second abdominal-shaped layer, a heart-shaped layer, and a rib bones shaped layer;
   (e) wherein the phantom further includes additional metallic layers and all metallic layers are disposed within said radiolucent material in the following order: a first backing layer, a first lung backing layer, a first lung-shaped outline defining layer, a second lung-shaped outline defining layer, a first abdominal-shaped layer, a second abdominal-shaped layer, a heart-shaped layer, a rib bones shaped layer, a second lung backing layer, and a second backing layer; and
   (f) wherein the first backing layer, the second backing layer, and the rib bones shaped layer each comprises aluminum, and the first lung backing layer, the second lung backing layer, the first lung-shaped outline defining layer, the second lung-shaped outline defining layer, the first abdominal-shaped layer, the second abdominal-shaped layer, and the heart-shaped layer each comprises copper.

3. An anatomic X-ray phantom for use with an X-ray imaging system, comprising:
   (a) a radiolucent material;
   (b) at least one layer of material of a shape regionally similar to a corresponding human anatomy portion and having X-ray absorptive characteristics similar to the corresponding human anatomy portion, and being disposed within said radiolucent material;
   (c) at least one test pattern adapted for X-ray quality assurance of the X-ray system when the phantom is in use with the X-ray system and being positioned inside the phantom in an area having radiopacity/radiolucency characteristics similar to the corresponding human anatomy portion;
   (d) wherein the phantom contains a plurality of human anatomy-shaped metallic layers disposed within said radiolucent material in the following order: a first lung-shaped outline defining layer, a second lung-shaped outline defining layer, a first abdominal-shaped layer, a second abdominal-shaped layer, a heart-shaped layer, and a rib bones shaped layer;
   (e) wherein the phantom further includes additional metallic layers and all metallic layers are disposed within said radiolucent material in the following order: a first backing layer, a first lung backing layer, a first lung-shaped outline defining layer, a second lung-shaped outline defining layer, a first abdominal-shaped layer, a second abdominal-shaped layer, a heart-shaped layer, a rib bones shaped layer, a second lung backing layer, and a second backing layer; and
   (f) wherein the at least one test pattern is directly adhered to a metallic layer on a side thereof which will face the X-ray system when the phantom is in use with the X-ray system.

4. An anatomic X-ray phantom for use with an X-ray imaging system, comprising:
   (a) a radiolucent material;
   (b) at least one layer of material of a shape regionally similar to a corresponding human anatomy portion and having X-ray absorptive characteristics similar to the corresponding human anatomy portion, and being disposed within said radiolucent material;
   (c) at least one test pattern adapted for X-ray quality assurance of the X-ray system when the phantom is in use with the X-ray system and being positioned inside the phantom in an area having radiopacity/radiolucency characteristics similar to the corresponding human anatomy portion;
   (d) wherein the phantom contains a plurality of human anatomy-shaped metallic layers disposed within said radiolucent material in the following order: a first lung-shaped outline defining layer, a second lung-shaped outline defining layer, a first abdominal-shaped layer, a second abdominal-shaped layer, a heart-shaped layer, and a rib bones shaped layer;

(e) wherein the phantom further includes additional metallic layers and all metallic layers are disposed within said radiolucent material in the following order: a first backing layer, a first lung backing layer, a first lung-shaped outline defining layer, a second lung-shaped outline defining layer, a first abdominal-shaped layer, a second abdominal-shaped layer, a heart-shaped layer, a rib bones shaped layer, a second lung backing layer, and a second backing layer; and (f) wherein the phantom includes a first, a second, and a third test pattern, wherein the first test pattern is directly adhered to the heart-shaped layer, the second test pattern is directly adhered to the first lung backing layer, and the third test pattern is directly adhered to the second abdominal-shaped layer.

5. An anatomic X-ray phantom for use with an X-ray imaging system, comprising:

(a) a radiolucent material;

(b) at least one layer of material of a shape regionally similar to a corresponding human anatomy portion and having X-ray absorptive characteristics similar to the corresponding human anatomy portion, and being disposed within said radiolucent material;

(c) at least one test pattern adapted for X-ray quality assurance of the X-ray system when the phantom is in use with the X-ray system and being positioned inside the phantom in an area having radiopacity/radiolucency characteristics similar to the corresponding human anatomy portion;

(d) wherein the phantom contains a plurality of human anatomy-shaped metallic layers disposed within said radiolucent material in the following order: a first lung-shaped outline defining layer, a second lung-shaped outline defining layer, a first abdominal-shaped layer, a second abdominal-shaped layer, a heart-shaped layer, and a rib bones shaped layer;

(e) wherein the phantom further includes additional metallic layers and all metallic layers are disposed within said radiolucent material in the following order: a first backing layer, a first lung backing layer, a first lung-shaped outline defining layer, a second lung-shaped outline defining layer, a first abdominal-shaped layer, a second abdominal-shaped layer, a heart-shaped layer, a rib bones shaped layer, a second lung backing layer, and a second backing layer;

(f) wherein the phantom includes a first, a second, and a third test pattern, wherein the first test pattern is directly adhered to the heart-shaped layer, the second test pattern is directly adhered to the first lung backing layer, and the third test pattern is directly adhered to the second abdominal-shaped layer; and (g) a grid disposed between the second lung backing layer and the rib bones shaped layer, and the grid being adapted to serve to break up uniform transmission areas from the metallic layers, and the grid including three open spaces, each space being cut out of the grid in an appropriate size for reciprocal correspondence with the heart test pattern, the lung test pattern, and the abdominal test pattern, respectively.

6. An anatomic X-ray phantom for use with an X-ray imaging system, comprising:

(a) at least two layers of radiolucent material;

(b) a plurality of layers of material each of a shape regionally similar to a corresponding human anatomy portion and having X-ray absorptive characteristics similar to the corresponding human anatomy portions, and being disposed between said two radiolucent layers;

(c) a corresponding plurality of test patterns adapted for X-ray quality assurance of the X-ray system when the phantom is in use with the X-ray system and being positioned inside the phantom in areas having radiopacity/radiolucency characteristics similar to the corresponding human anatomy portion;

(d) wherein said plurality of human anatomy-shaped metallic layers disposed between the two radiolucent layers comprises in the following order: a first lung-shaped outline defining layer, a second lung-shaped outline defining layer, a first abdominal-shaped layer, a second abdominal-shaped layer, a heart-shaped layer, and a rib bones shaped layer; and (e) wherein the phantom further includes additional metallic layers and all metallic layers are disposed between the two radiolucent layers in the following order: a first backing layer, a first lung backing layer, a first lung-shaped outline defining layer, a second lung-shaped outline defining layer, a first abdominal-shaped layer, a second abdominal-shaped layer, a heart-shaped layer, a rib bones shaped layer, a second lung backing layer, and a second backing layer.

7. An anatomic X-ray phantom for use with an X-ray imaging system, comprising:

(a) at least two layers of radiolucent material;

(b) a plurality of layers of material each of a shape regionally similar to a corresponding human anatomy portion and having X-ray absorptive characteristics similar to the corresponding human anatomy portions, and being disposed between said two radiolucent layers;

(c) a corresponding plurality of test patterns adapted for X-ray quality assurance of the X-ray system when the phantom is in use with the X-ray system and being positioned inside the phantom in areas having radiopacity/radiolucency characteristics similar to the corresponding human anatomy portion;

(d) wherein said plurality of human anatomy-shaped metallic layers disposed between the two radiolucent layers comprises in the following order: a first lung-shaped outline defining layer, a second lung-shaped outline defining layer, a first abdominal-shaped layer, a second abdominal-shaped layer, a heart-shaped layer, and a rib bones shaped layer;

(e) wherein the phantom further includes additional metallic layers and all metallic layers are disposed between the two radiolucent layers in the following order: a first backing layer, a first lung backing layer, a first lung-shaped outline defining layer, a second lung-shaped outline defining layer, a first abdominal-shaped layer, a second abdominal-shaped layer, a heart-shaped layer, a rib bones shaped layer, a second lung backing layer, and a second backing layer; and (f) wherein the first backing layer, the second backing layer, and the rib bones shaped layer each comprises aluminum, and the first lung backing layer, the second lung backing layer, the first lung-shaped outline defining layer, the second lung-shaped outline defining layer, the first abdominal-shaped layer, the second abdominal-shaped layer, and the heart-shaped layer each comprises copper.

8. An anatomic X-ray phantom for use with an X-ray imaging system, comprising:

(a) at least two layers of radiolucent material;

(b) a plurality of layers of material each of a shape regionally similar to a corresponding human anatomy portion and having X-ray absorptive characteristics similar to the corresponding human anatomy portions, and being disposed between said two radiolucent layers;

(c) a corresponding plurality of test patterns adapted for X-ray quality assurance of the X-ray system when the phantom is in use with the X-ray system and being positioned inside the phantom in areas having radiopacity/radiolucency characteristics similar to the corresponding human anatomy portion;

(d) wherein said plurality of human anatomy-shaped metallic layers disposed between the two radiolucent layers comprises in the following order: a first lung-shaped outline defining layer, a second lung-shaped outline defining layer, a first abdominal-shaped layer, a second abdominal-shaped layer, a heart-shaped layer, and a rib bones shaped layer;

(e) wherein the phantom further includes additional metallic layers and all metallic layers are disposed between the two radiolucent layers in the following order: a first backing layer, a first lung backing layer, a first lung-shaped outline defining layer, a second lung-shaped outline defining layer, a first abdominal-shaped layer, a second abdominal-shaped layer, a heart-shaped layer, a rib bones shaped layer, a second lung backing layer, and a second backing layer; and (f) wherein the phantom includes a first, a second, and a third test pattern, wherein the first test pattern is directly adhered to the heart-shaped layer, the second test pattern is directly adhered to the first lung backing layer, and the third test pattern is directly adhered to the second abdominal-shaped layer.

9. An anatomic X-ray phantom for use with an X-ray imaging system, comprising:

(a) at least two layers of radiolucent material;

(b) a plurality of layers of material each of a shape regionally similar to a corresponding human anatomy portion and having X-ray absorptive characteristics similar to the corresponding human anatomy portions, and being disposed between said two radiolucent layers;

(c) a corresponding plurality of test patterns adapted for X-ray quality assurance of the X-ray system when the phantom is in use with the X-ray system and being positioned inside the phantom in areas having radiopacity/radiolucency characteristics similar to the corresponding human anatomy portion;

(d) wherein said plurality of human anatomy-shaped metallic layers disposed between the two radiolucent layers comprises in the following order: a first lung-shaped outline defining layer, a second lung-shaped outline defining layer, a first abdominal-shaped layer, a second abdominal-shaped layer, a heart-shaped layer, and a rib bones shaped layer;

(e) wherein the phantom further includes additional metallic layers and all metallic layers are disposed between the two radiolucent layers in the following order: a first backing layer, a first lung backing layer, a first lung-shaped outline defining layer, a second lung-shaped outline defining layer, a first abdominal-shaped layer, a second abdominal-shaped layer, a heart-shaped layer, a rib bones shaped layer, a second lung backing layer, and a second backing layer;

(f) wherein the phantom includes a first, a second, and a third test pattern, wherein the first test pattern is directly adhered to the heart-shaped layer, the second test pattern is directly adhered to the first lung backing layer, and the third test pattern is directly adhered to the second abdominal-shaped layer; and (g) a grid disposed between the second lung backing layer and the rib bones shaped layer, and the grid being adapted to serve to break up uniform transmission areas from the metallic layers, and the grid including a plurality of open spaces, each space being cut out of the grid in an appropriate size for reciprocal correspondence with a corresponding one of said three test patterns.

* * * * *